(12) United States Patent
Sassoon

(10) Patent No.: US 7,878,371 B2
(45) Date of Patent: Feb. 1, 2011

(54) CONTROLLABLE DOOR HANDLE SANITIZER

(75) Inventor: Simon Sassoon, New York, NY (US)

(73) Assignee: Hyso Technology LLC, Carlstadt, NJ (US)

( * ) Notice: Subject to any disclaimer, the term of this patent is extended or adjusted under 35 U.S.C. 154(b) by 71 days.

(21) Appl. No.: 12/464,716

(22) Filed: May 12, 2009

(65) Prior Publication Data
US 2010/0051641 A1 Mar. 4, 2010

Related U.S. Application Data

(60) Provisional application No. 61/094,246, filed on Sep. 4, 2008.

(51) Int. Cl.
*B67D 1/00* (2006.01)
(52) U.S. Cl. ............... 222/52; 222/61; 222/183; 222/325; 222/402.1; 222/504; 222/645; 222/649; 422/28
(58) Field of Classification Search ............... 222/52, 222/61, 63, 644–645, 649, 183, 160, 165, 222/402.1, 504, 325, 192, 638–639, 181.3, 222/402.2, 648, 509; 422/28; 16/904
See application file for complete search history.

(56) References Cited

U.S. PATENT DOCUMENTS

| | | | |
|---|---|---|---|
| 1,491,780 A | | 4/1924 | Abbott |
| 1,783,097 A | | 11/1930 | Polcari |
| 2,527,955 A | | 10/1950 | Pagel |
| 3,314,746 A | | 4/1967 | Millar |
| 3,321,107 A | * | 5/1967 | Govin et al. ............ 222/2 |
| 3,584,766 A | | 6/1971 | Hart et al. |
| 3,589,563 A | | 6/1971 | Carragan et al. |
| 3,610,471 A | | 10/1971 | Werner |
| 3,615,041 A | | 10/1971 | Bischoff |
| 3,726,437 A | | 4/1973 | Siegel |
| 3,732,509 A | | 5/1973 | Florant et al. |
| 3,739,944 A | | 6/1973 | Rogerson |
| 3,779,425 A | | 12/1973 | Werner |
| 3,841,525 A | | 10/1974 | Siegel |

(Continued)

FOREIGN PATENT DOCUMENTS

FR 2848590 6/2004

(Continued)

*Primary Examiner*—Frederick C. Nicolas
(74) *Attorney, Agent, or Firm*—Leason Ellis LLP

(57) ABSTRACT

A controllable door handle sanitizer includes a base and an outer housing coupled to the base and movable between an open and a closed position. The sanitizer also includes a holder that receives and holds a container that stores a germicide and includes a first valve member. The holder is coupled to the base such that when the outer housing is opened, the container can be inserted and removed. The holder includes a biasing mechanism for applying a biasing force against the container to maintain the container in a fully loaded position. The sanitizer also includes an electronic valve module that includes a housing that is coupled to the base by engaging locating and support members integrally formed as part of the base. The module is positioned relative to the holder such that in the fully loaded position, the first valve member is actuated and opened, whereby discharge of the germicide is determined by an operating state of a second valve member of the electronic valve module.

12 Claims, 7 Drawing Sheets

U.S. PATENT DOCUMENTS

| | | | |
|---|---|---|---|
| 3,865,275 A | 2/1975 | De Nunzio |
| 3,899,105 A | 8/1975 | Fegley et al. |
| 3,994,440 A | 11/1976 | Mancini |
| RE29,117 E | 1/1977 | Sahajian et al. |
| 4,064,573 A | 12/1977 | Calderone |
| 4,171,776 A | 10/1979 | Pagliaro |
| 4,625,342 A | 12/1986 | Gangnath et al. |
| 4,832,942 A | 5/1989 | Crace |
| 5,016,781 A | 5/1991 | Ten Wolde et al. |
| 5,031,252 A | 7/1991 | Oyama et al. |
| 5,314,668 A | 5/1994 | Biermaier et al. |
| RE34,847 E | 2/1995 | Muderlak et al. |
| 5,676,283 A | 10/1997 | Wang |
| 5,695,091 A | 12/1997 | Winings et al. |
| 5,808,553 A | 9/1998 | Cunningham |
| 5,887,759 A | 3/1999 | Ayigbe |
| 6,029,600 A | 2/2000 | Davis |
| 6,123,268 A | 9/2000 | Chastine |
| 6,142,339 A | 11/2000 | Blacker et al. |
| 6,216,925 B1 * | 4/2001 | Garon ........................ 222/645 |
| 6,264,548 B1 | 7/2001 | Payne, Jr. et al. |
| 6,276,574 B1 | 8/2001 | Smrt |
| 6,279,777 B1 | 8/2001 | Goodin et al. |
| 6,298,521 B1 | 10/2001 | Butterfield |
| 6,533,141 B1 * | 3/2003 | Petterson et al. ................ 222/1 |
| 6,540,155 B1 * | 4/2003 | Yahav ......................... 239/70 |
| 6,645,435 B2 | 11/2003 | Dawson et al. |
| 6,789,695 B1 | 9/2004 | Gaudreau |
| 6,874,697 B2 | 4/2005 | Callueng |
| 7,320,418 B2 | 1/2008 | Sassoon |
| 7,360,674 B2 | 4/2008 | Sassoon |
| 2004/0026530 A1 | 2/2004 | Callueng |
| 2005/0112022 A1 | 5/2005 | Morgan |

FOREIGN PATENT DOCUMENTS

| | | |
|---|---|---|
| GB | 2418857 | 4/2006 |

* cited by examiner

CONTROLLABLE DOOR HANDLE SANITIZER

CROSS-REFERENCE TO RELATED APPLICATION

The present application claims the benefit of U.S. patent application Ser. No. 61/094,246, filed Sep. 4, 2008, which is hereby incorporated by reference in its entirety.

TECHNICAL FIELD

The present invention relates to an apparatus and method for rendering germ-free (sanitizing) door handles, and more particularly, to a device for dispensing a germicide, such as a disinfectant, antibacterial solution or cleansing agent, onto a door handle at controlled intervals and to a valve attachment suitable for use therewith.

BACKGROUND

Many people are reluctant to use public restrooms due to actual or perceived sanitary conditions of those restrooms. However, in some instances, such use is unavoidable.

These people try to avoid touching any surface after they have washed their hands. However, touching a surface of the restroom is nearly unavoidable because sometimes the person must touch the handle of the door to exit the restroom. Some people carry gloves, wipes or the like to use in such public restrooms. Some people take an extra paper towel to use to cover the door handle. All of these techniques work, but are burdensome and not efficient.

Some prior art methods suggest covering a handle of a door so a person opening the door can avoid direct contact with the handle. Covering a door handle, while effective in preventing a person from contacting the door handle during operation of the door, does little to clean or disinfect the door handle. Furthermore, the cover then becomes a source of contamination, germs, bacteria and the like. Therefore, there is a need for efficiently and effectively sanitizing the handle of a door. This typically requires a person to carry a liquid spray bottle into a room, spray a disinfectant or antibacterial liquid onto the door handle and then wipe the handle clean. This procedure can be cumbersome and inefficient, requiring a person to carry items with him or her for the cleaning procedure.

Still further, some people, often nicknamed germephobes, wonder when the last time a door handle was cleaned, and even if there is some form of protection for this person, they are uncomfortable touching the door handle. These people are not satisfied by the mere existence of some means for cleaning or sanitizing the door handle, rather, they might prefer to know that such a cleansing device is activated at intervals in response to certain conditions or according to a prescribed cleaning schedule, such as every several minutes. Therefore, there is a need for efficiently cleaning and sanitizing a door handle at prescribed time intervals in response to certain conditions, e.g., according to a predetermined cleaning schedule, opening and closing of the door, passing of an individual in the vicinity of the door knob, turning on/off of the lights, etc. There is also a need to control the door handle sanitizing device to automatically shutdown during times when the door is not in use, e.g., overnight, weekends, and any other prescribed time when the door is not being use for an extending period. There is also a need to provide an efficient, compact and effective spray actuator that is part of the cleansing device.

SUMMARY

A controllable door handle sanitizer includes a base and an outer housing coupled to the base and movable between an open and a closed position. The sanitizer also includes a holder that receives and holds a container that stores a germicide and includes a first valve member. The holder is coupled to the base such that when the outer housing is opened, the container can be inserted and removed. The holder includes a biasing mechanism for applying a biasing force against the container to maintain the container in a fully loaded position. The sanitizer also includes an electronic valve module that includes a housing that is coupled to the base by engaging locating and support members integrally formed as part of the base. The module is positioned relative to the holder such that in the fully loaded position, the first valve member is actuated and opened, whereby discharge of the germicide is determined by an operating state of a second valve member of the electronic valve module.

In another embodiment, a controllable door handle sanitizer includes a base and an outer housing coupled to the base and movable between an open and a closed position. The sanitizer also includes a holder that receives and holds a container that stores a germicide. The container has a first valve member and the holder is coupled to the base such that when the outer housing is opened, the container can be inserted and removed. The sanitizer further includes an electronic valve module that includes a housing that is coupled to the base. The module is positioned relative to the holder such that when the container is in a fully loaded position with respect to the holder and the holder is disposed in a loaded position within the base, the first valve member is disposed within an inlet of the electronic valve module and assumes an actuated and opened position, whereby discharge of the germicide from the sanitizer is determined by an operating state of a second valve member of the electronic valve module that is located downstream of the first valve member and in fluid communication thereof. A controller is included as part of the sanitizer and includes a power source for controlling operation of the sanitizer. The electronic valve module is operatively coupled to the controller such that the controller selectively signals the second valve member to open and close depending upon on user inputted operating selections that control when the germicide is discharged.

These and other aspects, features and advantages shall be apparent from the accompanying Drawings and description of certain embodiments of the invention.

BRIEF DESCRIPTION OF THE DRAWINGS

The present invention is illustrated by way of example and not by way of limitation in the figures of the accompanying drawings in which like references indicate similar elements.

DETAILED DESCRIPTION OF CERTAIN EMBODIMENTS OF THE INVENTION

Figure 1:
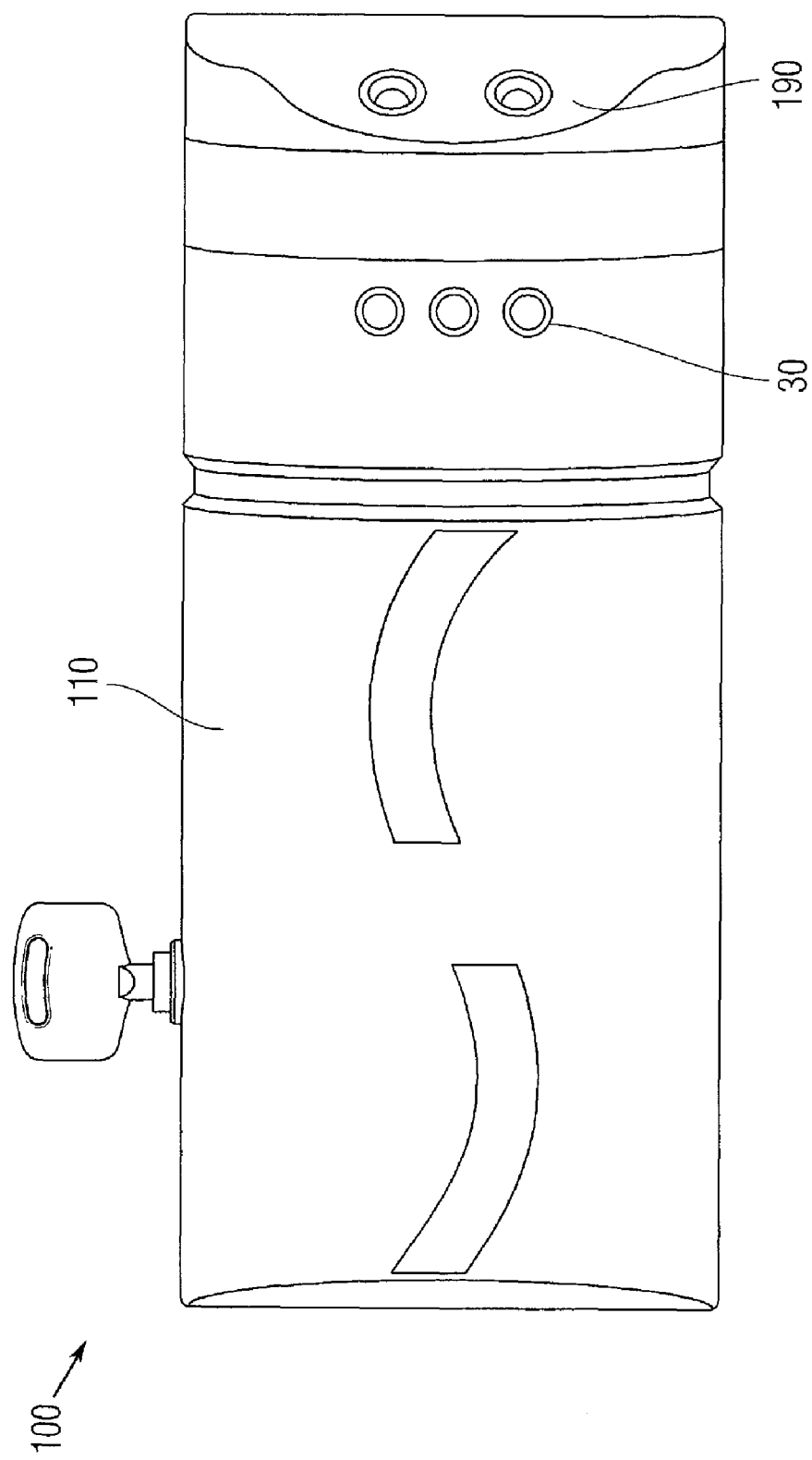
FIG. 1 is a front elevation view of a door handle sanitizer according to a first embodiment of the present invention.

The general design and function of one spray dispenser for a door are disclosed in commonly assigned U.S. Pat. No. 7,320,418, which is hereby incorporated by reference in its entirety.

In accordance with the present invention and as shown in FIGS. 1-4, a spray dispenser 100 in accordance with a first embodiment is shown. The spray dispenser 100 is operable to spray a germicide 10 therefrom to coat, and thereby sanitize an outwardly extending door handle. Referring to FIGS. 1-4, the spray dispenser 100 includes an outer housing or cover 110, a base 200, user accessible control switches 20 and visible indicator lights 30 for providing control and status information of the dispenser 100. The spray dispenser 100 is mounted to the door above the door handler to permit the sprayed germicide to travel down and coat the handle.

The outer housing 110 can be coupled to the base 200 in any number of different ways that allow the outer housing 110 to be opened relative to the base 200. For example, the outer housing 110 can be pivotally or hingedly coupled to the base and in one embodiment, the outer housing 110 is hingedly connected to the base 200 via prongs a top end thereof. In a closed position, the outer housing 110 completely conceals the internal components of the dispenser 100, while in the opened position, the outer housing 110 provides access to a germicide source 300 as well as other internal components contained within the dispenser 100, such as a power source (e.g., one or more batteries 301).

In addition, the outer housing 110 can be lockingly coupled to the base 200 using a lock mechanism 50. The lock mechanism 50 can be any number of different lock mechanisms that allow the outer housing 110 to be securely attached to the base 200 when the lock mechanism 50 is placed in a locked position. For example and as shown, the lock mechanism 50 can be a key based latch mechanism that includes an assembly that is inserted into an opening 201 that is formed in the base 200. The assembly includes a key 52 and a base plate 54 that includes a section 55 that is inserted into and is assessable through the opening 201. The base plate 54 includes a first part 57 and a second part 59 that includes the section 55. A hole 54 formed in the section 55 receives a lock part 63 that receives the key 52. The lock part 63 can include one or more tabs extending radially outward such that when the lock part 63 rotates in the hole 54 due to rotation of the key 52, the position of the tabs changes to effectuate unlocking and locking of the outer housing 110. The first part 57 is coupled to a side wall of the base 200 and includes a slot 61 formed along one edge thereof. The second part 59 includes a prong 63 that is sized so that it can be received in the slot 61. To lock and unlock the outer housing 110 from the base 200, the user simply inserts the key 52 through the opening 201 and into the hole 54 and then rotates the key 52 to cause the inner workings of the lock mechanism 50 to move and disengage from the outer housing 110 as in the case of unlocking the outer housing 110 from the base 200. To lock the outer housing 110 to the base 200, the outer housing 110 is placed back on the base 200 and the process is reversed resulting in the engagement of the outer housing 110 to the base 200.

In this embodiment, the outer housing 110 does not have to be hingedly coupled to the base 200 but instead the outer housing 110 can be a separate part that is removable (detachable) from the base 200 when the lock mechanism 50 is in an unlocked position. Alternatively, the outer housing 110 can be hingedly connected along one side so that the outer housing 110 opens and closes like a traditional door as opposed to opening and closing along the top (up and down manner).

The outer housing 110 of the spray dispenser 100 includes a top wall 112, a bottom wall 120 and, for the purpose of presenting a pleasant appearance, a curved front wall 130. The outer housing 110 has a pair of side edges 111 that extend between the top wall 112 and the bottom wall 120. The side edge 111 is not a straight edge but instead is irregular in that it includes a notch (U-shaped) 113 that aligns with the lock mechanism 50 when the outer housing 110 is mated to the base 200. The outer housing 110 can also include a protrusion 115 that mates with a grooved section of the base 200 to further locate and situate the outer housing 110 relative to the base 200.

The outer housing 110 is thus a hollow member that receives a number of the working components of the spray dispenser when the outer housing 110 is in the closed position.

The base 200 is also a generally hollow member that has a rear wall or surface 202, a bottom wall 204 and a pair of side walls 206. The top of the base 200 is substantially open; however, there is a small top wall or surface 208. The bottom wall 204 extends across between the side walls 206 and is joined to the rear wall 202. A top edge 209 of the rear wall 202 extends above the top wall 208. One side wall 206 includes the opening 201 and each of the side walls 206 has a construction that is complementary to the side edges 112 of the outer housing 110. Foe example, an outer surface of the side wall 206 can include a contoured, recessed section 210 that receives the side edge 112 of the outer housing 110. The recessed section 210 is defined by an edge 212 such that in the closed position, the edges 112, 212 abut one another for a clean appearance. The key hole area formed as part of the side wall 206 is received into the notch 113 of the side edge 112.

Figure 4:
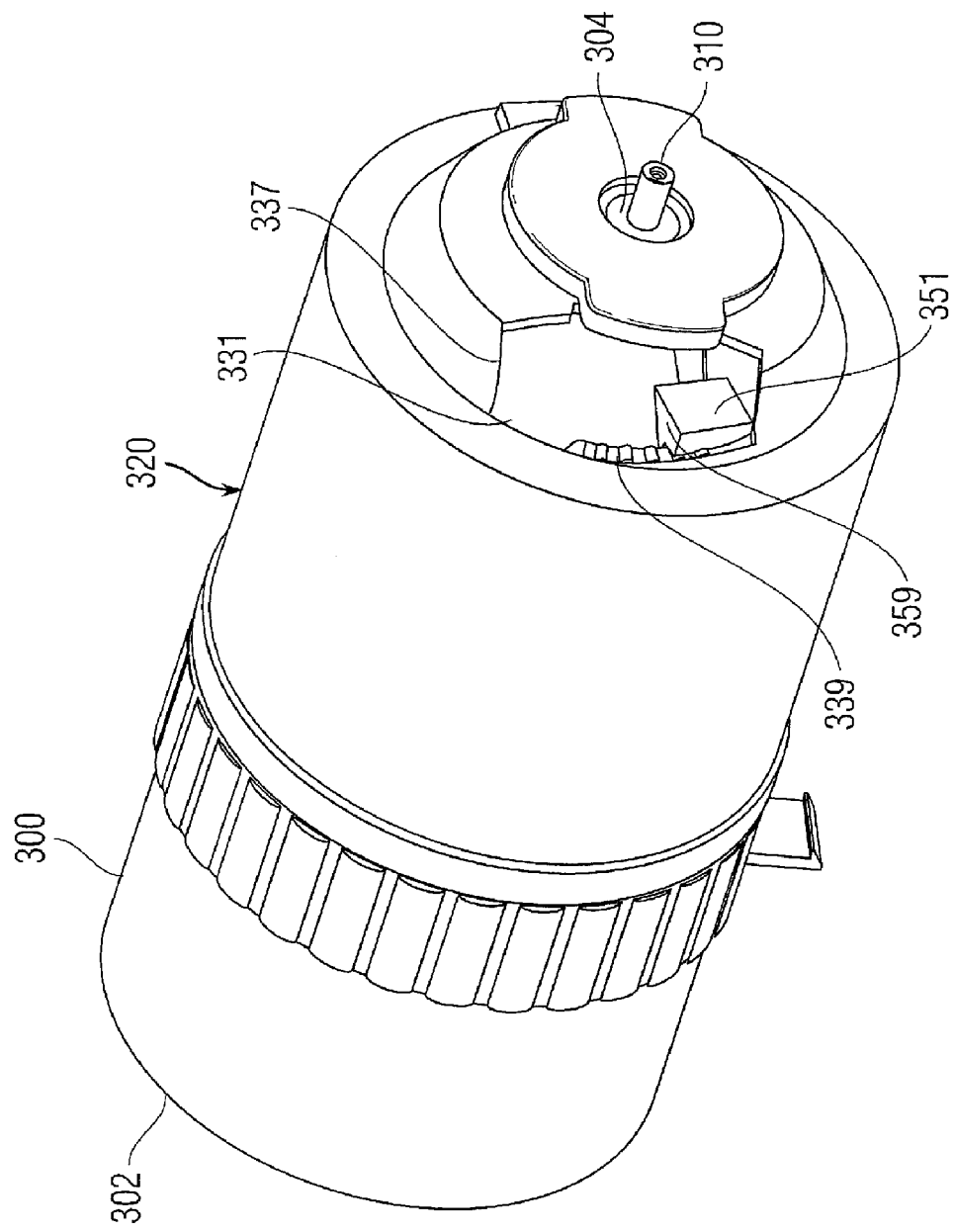
FIG. 4 is a perspective view of a cartridge or canister holding a fluid to be dispensed by the sanitizer of FIG. 1.

The spray dispenser 100 has a number of working components that permit the germicide to be selectively and controllably discharged from the dispenser 100 as described below. The germicide source 300, preferably in the form of an aerosol can, is removably mounted within spray dispenser 100. In particular, a germicide source 300 can be in the form of an elongated, round aerosol cartridge (can) 300 as shown in FIG. 4. The cartridge 300 has a first end 302 and an opposite second end 304. A valve member 310 is located at the second end 304 and is designed so that when the valve member 310 is actuated (pressed), the valve opens and stored germicide is released.

The dispenser 100 also includes a cartridge holder assembly 320 for holding the cartridge 300 (germicide source) in place within the interior of the dispenser 100. The assembly 320 includes an outer holder or sleeve member 330 and an inner holder or sleeve member 350. The inner sleeve member 350 is a hollow part that has an open top 352 and a partially closed bottom 354 and is sized and shaped to receive at least the second end 304 of the cartridge 300. As a result, the inner sleeve member 350 is a cup shaped member that includes a circular side wall. The cartridge 300 can interface with the inner sleeve member 350 in any number of different manners including a frictional fit. For example, the inner sleeve member 350 can fit over the shoulder of the cartridge 300.

In particular, an opening 353 at the bottom 354 is sized to receive at least the valve assembly 310 of the cartridge 300 such that the valve assembly 310 extends below the bottom 354. At or near the top 352, a plurality of ribs can be circumferentially arranged therearound. The inner sleeve member 350 can be formed a suitable plastic using conventional techniques, such as a molding process. At or near the bottom 354, the inner sleeve member 350 includes one or more locking tabs 351 best shown in FIG. 4. The locking tab 351 includes a locking surface 359 which engages a complementary portion of the outer sleeve member 320 as described below.

Similarly, the outer sleeve member 330 is a hollow part that has an open top 332 and a partially closed bottom 334 and is shaped and sized to receive both the inner sleeve member 350 and the cartridge 300 that is contained therein. As a result, the sleeve member 330 is a cup-shaped member that includes a circular shaped side wall 336. The bottom 334 includes an opening 335 that permits the valve member 310 of the cartridge 300 to be accessible and engageable. In other words, the valve member 310 passes through the opening 335. The outer sleeve member 330 can be coupled to the base 200 using conventional means, such as a mechanical fit, including use of prongs or the like 313 that snap fit into receiving portions of the base 200.

As previously mentioned, the inner and outer sleeve members 350, 330 selectively engage one another for locking the canister/cartridge in place within the holder assembly. For example and as shown in the drawings, the outer sleeve member 330 can include one or more (e.g. a pair) of notches or openings 337 formed in the bottom 334 of the outer sleeve member 330. In the illustrated embodiment, there are a pair of notches 337 formed opposite one another. Within the opening 337, the outer sleeve member 330 has a locking mechanism for selectively yet removable locking the inner sleeve member 350 to the outer sleeve member 330. For example, the locking mechanism can be in the form of a locking rail or edge 339 that is formed along an outer edge of the opening 337. The locking rail 339 includes a series of teeth that are formed along a length of the rail 339. There is a space 331 formed adjacent the locking rail 339, with the space 331 being free of any teeth.

The manner of locking the inner sleeve member 350 to the outer sleeve member 330 is now described. The space 331 is sized and constructed to receive the locking tab 351 that is fixedly formed as part of the inner sleeve member 350 at the bottom 354 thereof. When the inner sleeve member 350 is first inserted into the outer sleeve member 330, the locking tab 351 is aligned with the space 331. When received within the space 331, the locking tab 351 and in particular, the locking surface 359 is located adjacent the teeth of the locking rail 339. The teeth and locking tab are complementary to one another and engage one another in a ratcheting manner in that as the inner sleeve member 350 is rotated (or the cartridge 300 is rotated), the locking surface 359 of the locking tab 351 begins to ride along the locking rail 339 and engage the teeth thereof, thereby securely locking the inner sleeve member 350 in place relative to the outer sleeve member 330. The locking tab 351 thus can function as a pawl of a ratcheting mechanism as it engages the teeth of the locking rail 339. It will therefore be appreciated that the cartridge 300 is securely locked in place in an engaged state by simply inserting the inner sleeve member 350 to which the cartridge 300 is mated into the outer sleeve member 330 in a properly aligned manner and then rotating the inner members relative to the outer sleeve member 330 to cause a locking therebetween. To remove the cartridge 300 as when it is empty, the locking tab 351 is disengaged from the locking rail 339 and the inner sleeve member 350 is rotated in an opposite direction until the locking tab 351 aligns with the space 331 to permit removal of the inner sleeve member 350 and cartridge 300. Other techniques can be used to remove the cartridge 300.

This locking results in the cartridge 300 being properly loaded and the valve assembly 310 is in the proper orientation.

In one embodiment, the cartridge 300 is locked in place by first inserting it into the inner sleeve member 350 and then inserting the inner sleeve member 350 into the outer sleeve member 330 and pushing the cartridge 300 down and then rotating the inner sleeve member 350 relative to the outer sleeve member 330 to cause a locking therebetween. This type of action is similar to the opening and locking of a childproof pill bottle where a force is applied to the cap and the cap is then rotated to cause locking.

The dispenser 100 also includes a spray actuator 400 that controls the regulation and spraying of the germicide. In accordance with the present invention, the actuator 400 is in the form of an electronic valve module 500 that includes a controllable valve, a processor (circuit board) 520, a power source (batteries 301) and can include the user accessible control switches 20 and the visible indicator lights 30. In the illustrated embodiment, the actuator 400 has a partially hollow body or housing 410 that is generally square or rectangular shaped and includes a rear wall 412, a partially open front wall 414 and opposing side walls 416. An outer surface of the side walls 416 stores the power source 301 (batteries) and in particular, the outer surface of each of the side walls 416 can include a compartment 421 that receives and includes the power source 301 which is in the form of one or more batteries. In the illustrated embodiment, each side wall 416 includes one compartment 421 that each stores a pair of batteries 301. The actuator 400 has a hollow interior compartment or space 401 that has a top portion that receives the partially closed bottom 334 of the outer sleeve member 330 and allows the germicide to be dispensed as described below.

The actuator 400 also includes the electronic valve module 500 that includes the controllable valve and the processor (circuit board) 520. For example, electronic valve module 500 can be a solenoid and therefore, the valve is a solenoid valve. As is known, the valve is an electrochemical valve for use with liquid or gas controlled by running or stopping an electrical current through a solenoid, which is a coil of wire, thus changing the state of the valve. The electronic valve module 500 is designed to be received and contained within the actuator housing 410 within the hollow interior space 401. The electronic valve module 500 has an inlet 540 that receives the liquid or gas, in this case, the discharged germicide, and an opposite outlet 550 with the solenoid valve being formed between the inlet 540 and the outlet 550. Accordingly, when the valve position is in the open position, the discharged germicide can flow into, through and out of the outlet 550 and conversely, when the valve is closed, the discharged germicide is prevented from flowing into the outlet 550.

The actuator 400 also includes a flow director 560 that includes a housing that receives the electronic valve module 500 and includes an outlet 562 (e.g., tubular shaped conduit) that receives the outlet 550 of the module 500 in such a way that the plume of the discharged germicide is not impeded with and more specifically, the outlet 562 and the outlet 550 both have round cavities or spaces that allow for the natural spray pattern of the germicide has it is discharged from the cartridge 300 through the valve of the module 500.

The processor (circuit board) 520 can be coupled to the body 410 and can extend across the open front wall 414. Electrical connection is made between the electronic valve module (solenoid) 500 and the power source 301 (batteries), thereby powering the electronic valve module 500 and selectively permit the solenoid valve to be opened and closed depending upon the operating state of the dispenser 100. The user accessible control switches 20 and the visible indicator lights 30 are also operatively connected to the processor 520 to permit control over the dispenser and allow the user to place the dispenser 100 in any number of different operating states as described below.

A control panel cover 580 can be provided for insertion over the user accessible control switches 20 and the visible indicator lights 30. The cover 580 has openings formed therein to permit the control switches 20 and the indicator lights 30 to be accessible and/or visible. The cover 580 is coupled to the actuator housing 410 using conventional means, e.g., snap-fit means. As shown, the body 410 can include a pair of posts 401 that are received into complementary openings 582 formed in the cover 580.

In yet another aspect of the present invention, the dispenser 100 has a sensing mechanism 190 incorporated therein to detect the presence of an unintended object underneath or in close proximity to the dispenser 100. When an unintended object is located too close to the dispenser 100 (within the sensing zone), the actuator 400 is not actuated while the unintended object remains within the sensing zone. For example, if a small child is standing underneath or is in close proximity to the dispenser 100, the sensing mechanism will detect such presence and if this detection event overlaps with a time when the dispenser is programmed to be actuated, the dispenser 100 will not spray germicide from the cartridge 300. Instead, the control program can be designed so that if the dispenser 100 is not actuated at the programmed time due to activation of the sensing mechanism, the program will wait a predetermined (programmed) time period before attempting again to actuate the actuator assembly and spray germicide. This process can continue until a successful actuation occurs and the germicide is sprayed.

Figure 2:
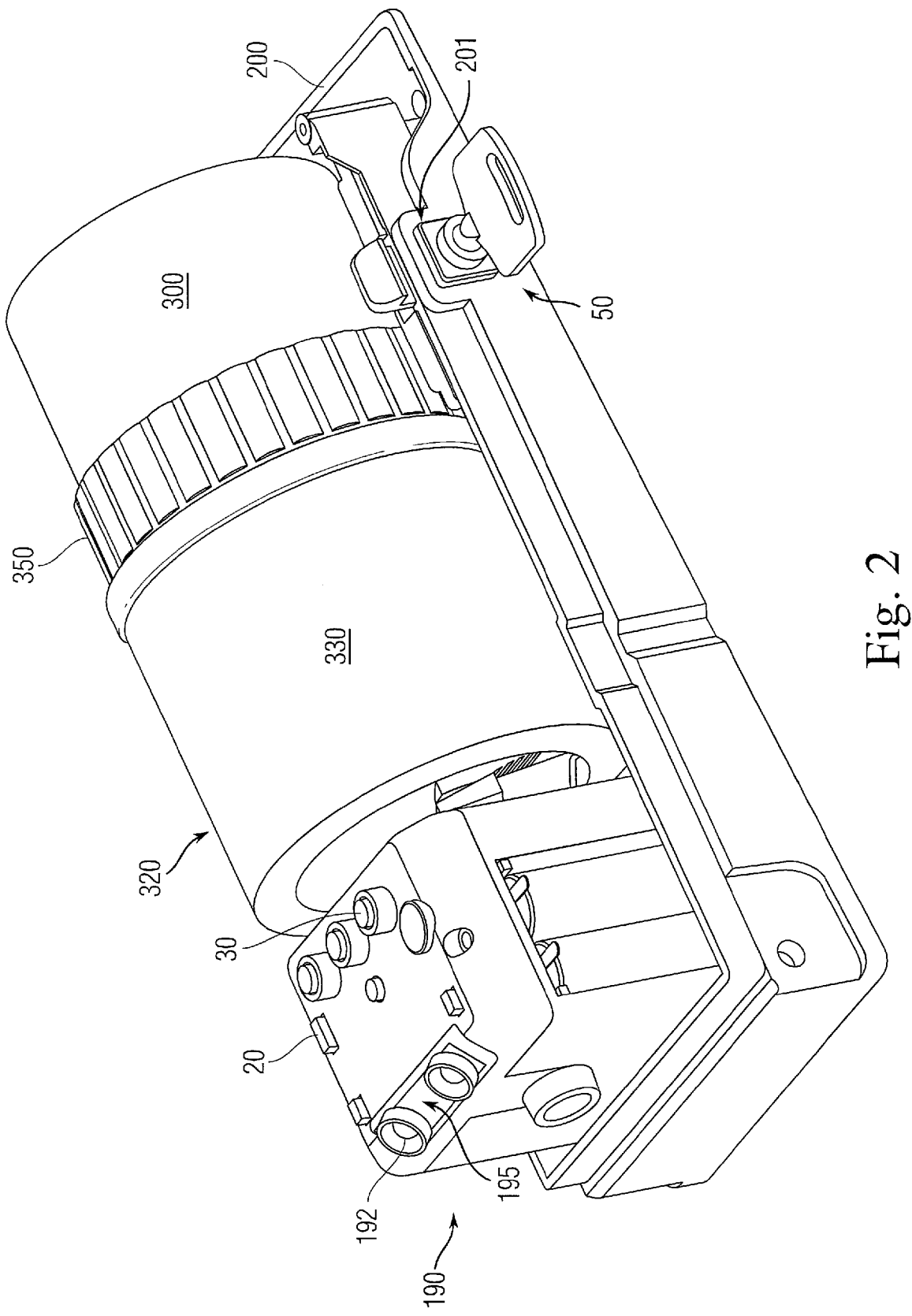
FIG. 2 is a side perspective view of the door handle sanitizer of FIG. 1 with a front cover thereof removed.
Figure 3:
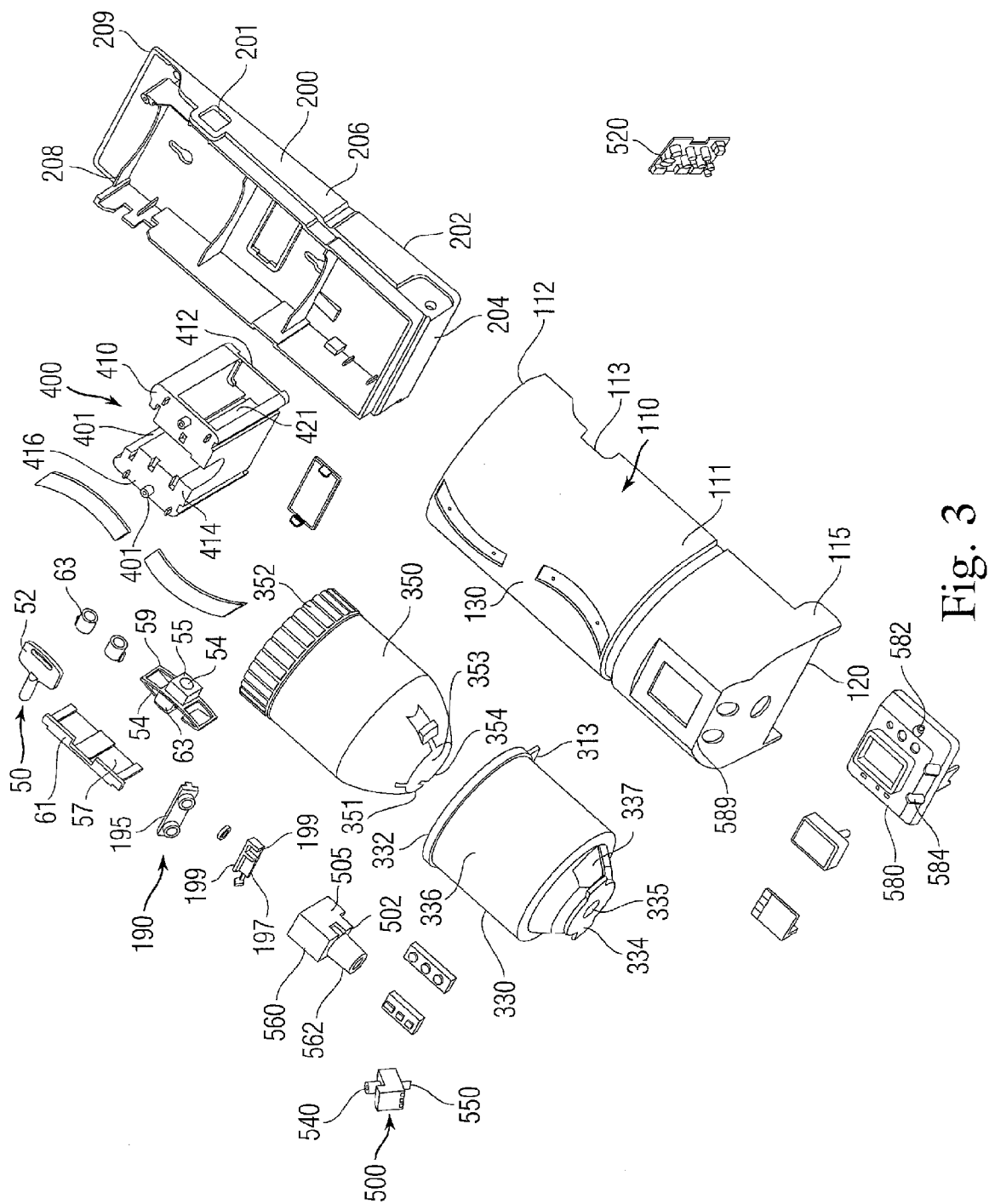
FIG. 3 is an exploded perspective view of the various parts of the sanitizer of FIG. 1.

The sensing mechanism 190 illustrated in the figures includes a pair of sensors 192 that are located at or near the bottom of the dispenser 100. In the illustrated embodiment, the sensing mechanism 190 is located proximate the other control features and PCB 520 of the dispenser 100. In particular and as shown in FIG. 2, the cover 580 can include openings 584 that accommodate the sensors 192. In addition to the sensors 192 themselves, the sensing mechanism 190 also includes a sensor cover 195 and a sensor base 197 that properly located and positions the sensors 192. The sensor base 197 includes a pair of slots or retaining structures 199 that receive and hold the sensors 192 at the proper angle. The sensors 192 can be set at 45 degree angles (relative to a vertical axis of the dispenser) and can be set at different angles and in different directions from one another resulting in an expanded scope of sensing coverage. The sensors 192 are operatively connected to the electronics (PCB and controller) of the dispenser 100 so that sensor signals are sent to the controller and under select conditions, such as when an unintended object is sensed by sensors 192, the controller controls operation of the actuator 400 so that the unintended object that is located close to the dispenser 100 is not sprayed with germicide. Since there are two sensors 192, the sensor cover 195 includes two openings to accommodate the sensors 192. The sensor cover 195 can be snap-fittingly engaged to the cover 580 to allow access to the sensors 192 in the case that access is needed. The main cover 130 also includes openings 589 that allow operation of the sensors 192 since the sensors 192 are axially aligned with the openings 589.

Any number of different sensors 192 can be used in the dispenser 100. For example, the sensors 192 can be in the form of motion sensors or can be sensors that detect an obstruction in a path thereof.

In one embodiment, the sensing mechanism 190 is configured so that it is capable of sensing an object that is located within one and half feet from the floor to the dispenser 100. This is sufficient to detect a small child or animal, etc.

The actuator 400 can be constructed to be removeably mated and securely coupled to the base 200. For example, the base 200 can include molded structures, e.g., ribs, etc., that guide and allow for the insertion of the actuator 400 into the base 200. Snap-fit type arrangements or fasteners can be used to couple the actuator 400 to the base 200.

As shown in FIG. 2, in the fully assembled condition, the electronic valve module 500 and most the actuator 400 are disposed below the outer sleeve member 330 and the inserted cartridge 300. It will be appreciated that the cartridge holder and the actuator 400 are complementary to one another and are positioned relative to one another such that when the cartridge 300 is disposed into the inner sleeve member 350 and is locked in place relative to the outer sleeve member 330, the valve member 310 of the cartridge 300 is inserted into the inlet 540 of the module 500 and this insertion causes the cartridge valve member 310 to be opened, thereby causing the germicide to be discharged from the cartridge 300 into the inlet 540. In other words, when the cartridge 300 is locked in place and the cartridge 300 is in the fully loaded position of FIG. 2, the valve member 310 thereof remains in an open position, thereby allowing the germicide to be discharged from the cartridge 300 into the electronic valve module 500. In other words, the loading of the cartridge 300 causes the valve assembly 310 to be moved into the open position. Whether or not the germicide is discharged from the dispenser 100 depends on the position of the solenoid valve. When the solenoid valve is opened, the germicide is discharged from the electronic valve module 500 by passing through the outlet 562 and through the flow director 560. The outlet 562 of the flow director 560 is aligned with the opening formed in the bottom wall 120 of the outer housing 110 and therefore, the spray freely emanates from the dispenser 100.

The control switches 20 and the indicator lights 30 can be similar or identical to those described in the previously incorporated '418 patent. In one embodiment, one control switch 20 is an on/off switch, one is a reset button, and there can be buttons to set the frequency of when the germicide is sprayed. For example, the one control switch 20 is a switch to set how often the germicide is sprayed and in particular, this switch 20 can be moved into a number of different time interval settings, such as 15 minutes, 30 minutes, and 60 minutes. To program the dispenser 100 to spray every 30 minutes, the control switch 20 is set to the 30 minute setting. The control switches are easily accessible once the front cover 130 is lifted or otherwise separated from the base 200. The indicator lights 30 can include a power on light, a light sensor indicator and a refill indicator that indicates replacement of the cartridge 300 is in order.

It will therefore be appreciated that in the embodiment of FIGS. 1-4, the loading of the cartridge assembly into the actuator assembly 400 results in the valve assembly 310 being permanently depressed and therefore, the valve assembly 310 itself does not have to be contacted or manipulated to cause a spraying of the germicide.

Figure 5:
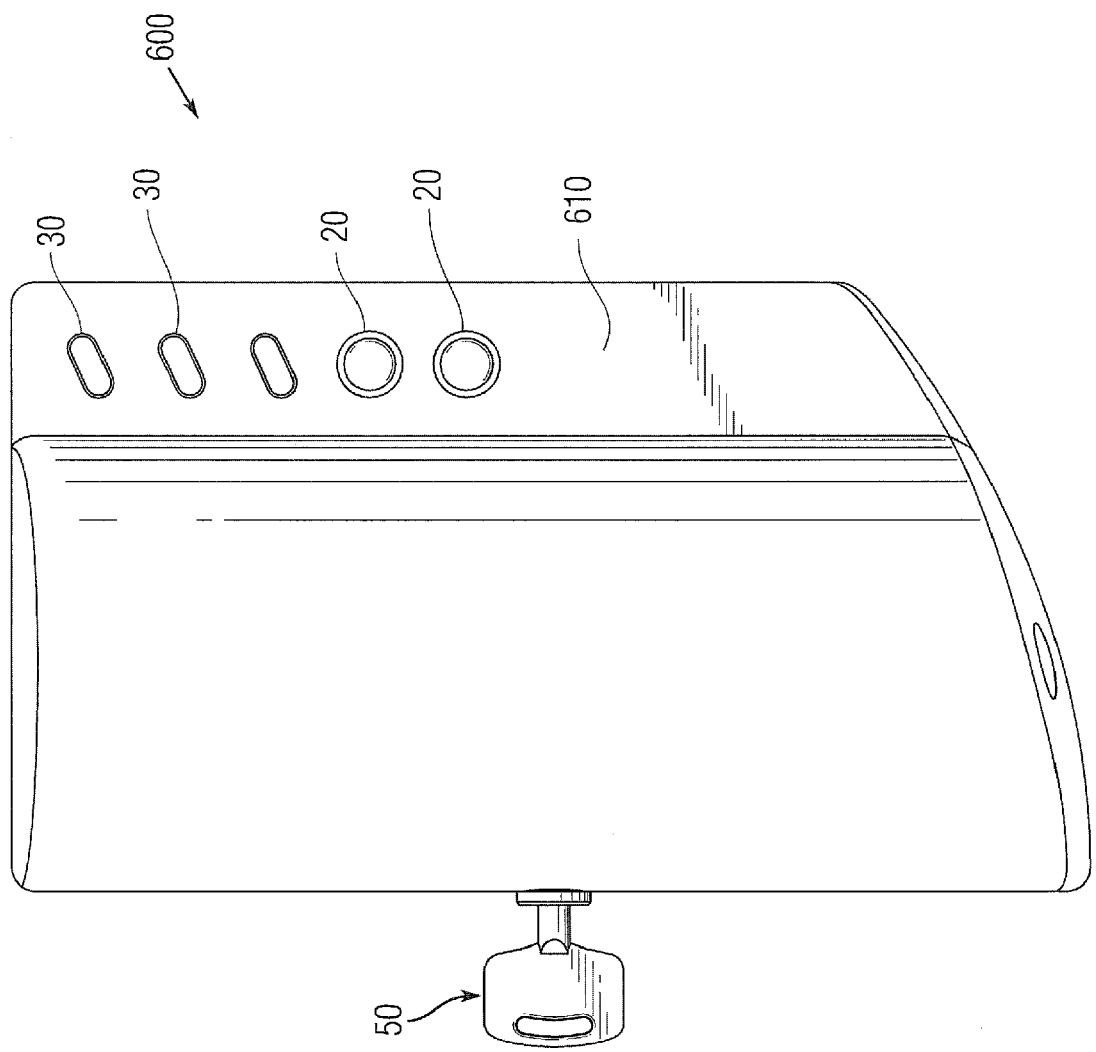
FIG. 5 is a front elevation view of a door handle sanitizer according to a second embodiment of the present invention.
Figure 6:
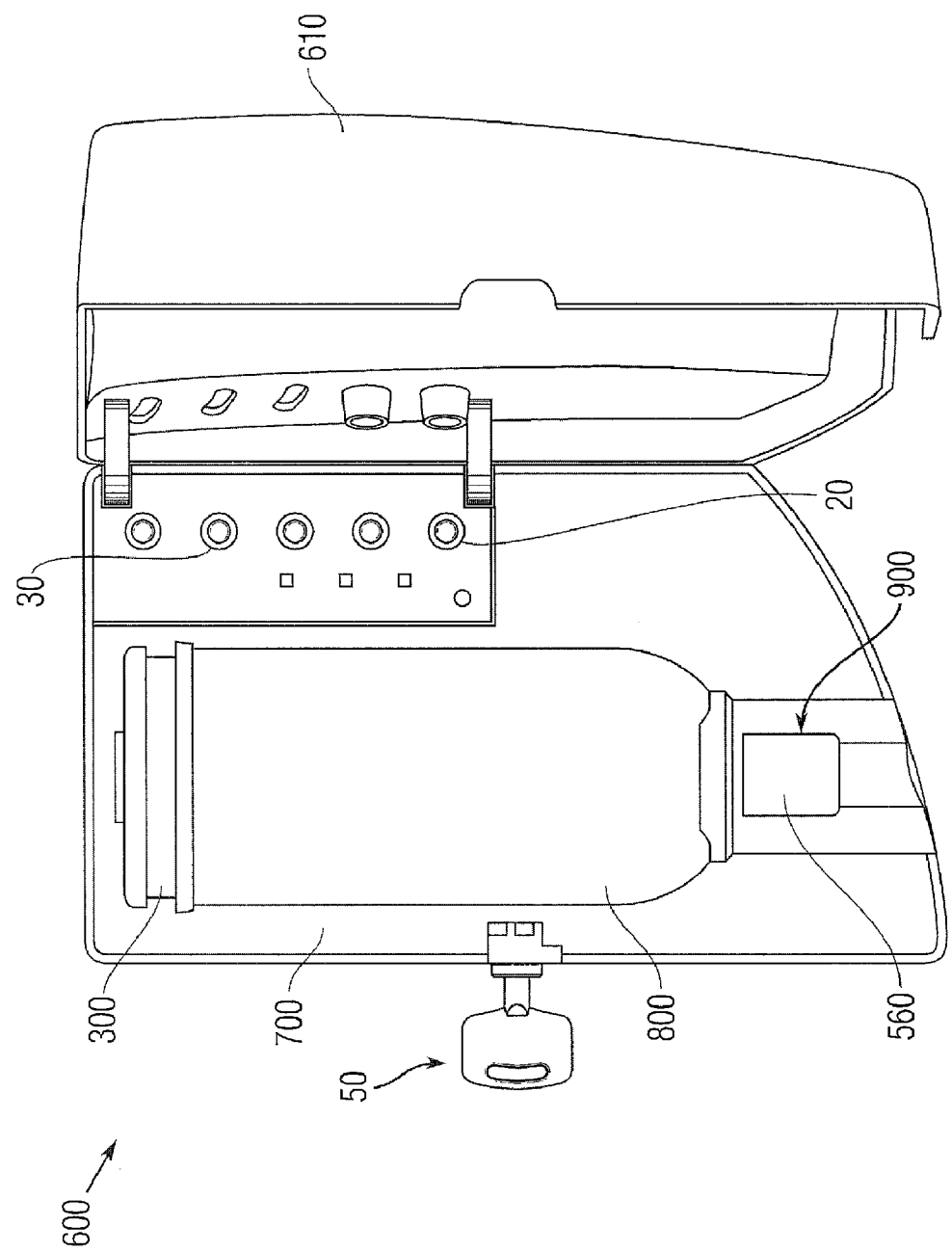
FIG. 6 is a front perspective view of the door handle sanitizer of FIG. 5 in an open position.
Figure 7:
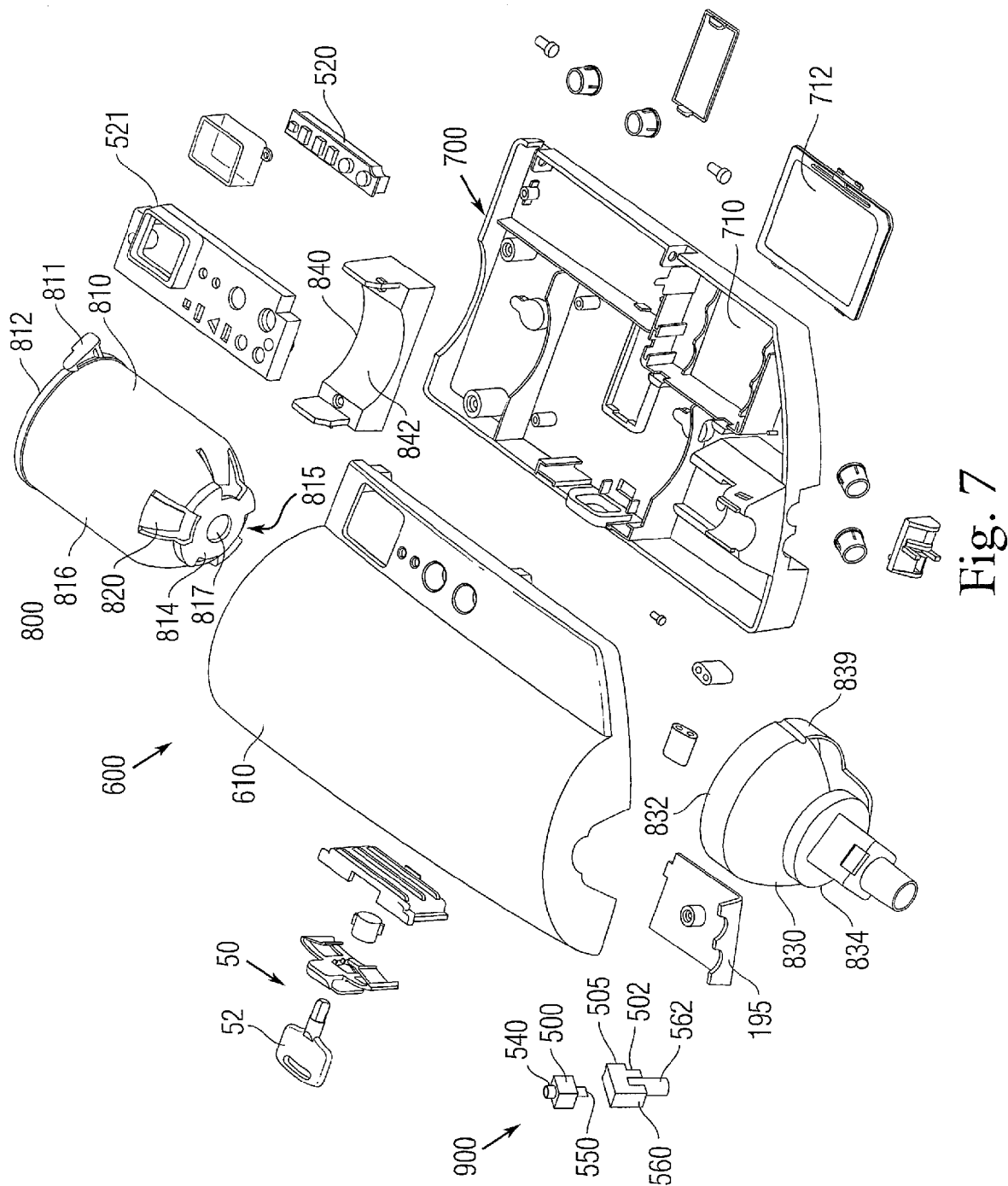
FIG. 7 is an exploded perspective view of the various parts of the sanitizer of FIG. 5.

Now referring to FIGS. 5-7 in which a spray dispenser 600 in accordance with a second embodiment is shown. Dispenser 600 is similar to dispenser 100 and therefore, like elements will not be described in great detail. In particular, the layout of the controls 20 and visual indicators 30 is different in the dispenser 600 and in particular, the controls 20 and indicators 30 are aligned in a vertical row as opposed to being arranged in rows. It will be appreciated that the operation and performance of the dispenser 600 is substantially the same or identical to the dispenser 100 with the main difference being the aesthetic look and design of each dispenser.

The dispenser 600 includes a number of the same or similar working components as the dispenser 100 including but not limited to an outer housing 610 and a base 700, lock mechanism 50, cartridge 300 and a cartridge holder assembly 800 and a dispenser actuator 900.

In this embodiment, the base 700 includes a number of integrally formed features (structures) that permit the other components of the dispenser to be secured thereto in a fixed location. For example, the base 700 can include an integral compartment 710 that stores the power source 301 (batteries). The compartment 710 is closed off with a door 712.

The cartridge holder assembly 800 is similar to the previously described holder assembly. In this embodiment, the holder assembly 800 is in the form of two parts, namely, a first upper part 810 and a second bottom part 830. The first upper part 810 is a cup shaped member that has an open top end 812 and a partially closed bottom end 814. A cylindrical side wall 816 provides the cup-shaped form of the first upper part 810.

The first upper part 810 includes a plurality of flexible fingers 820 that are arranged circumferentially about the bottom 814. The bottom 814 of the first upper part 810 has a series of notches or slots 815 that are circumferentially spaced about the bottom 814. Each finger 820 is axially aligned with the notch 815. The fingers 820 can serve to lock and engage the cartridge 300 in place within the first upper part 810.

The first upper part 810 also includes a part 811 that can be used to couple the first upper part 810 to another part, such as a structure that is part of or coupled to the base 700. For example, a holder 840 can be provided for retaining the first upper part 810 in place, with the holder 840 being mounted to the base 700. The holder 840 has a curved surface 842 that is complementary to the cylindrical side wall 816 of the first upper part 810.

The first upper part 810 is designed to mate with and securely hold the cartridge 300 in place similar to the first embodiment disclosed herein. For example, the cartridge 300 can be located in place within the interior of the first upper part 810 using the flexible fingers 820 or other means. For example, the cartridge 300 sits within the first upper part 810 with the bottom end 314 seated against the bottom of the first upper part 810 and the valve assembly 310 extends through the opening 817.

The second bottom part 830 is similarly a cup shaped member that has an open top 832 and a partially closed bottom 834. At the closed bottom end 834, an opening 835 is included and the body of the second bottom part 830 has a side opening or notch 839 formed therein. The second bottom part 830 is designed to securely mate with the first upper part 810 in a manner in which the valve assembly 310 passes through the opening 835 in the bottom part 830. Any number of different techniques can be used to mate the first upper part 810 with the second bottom part 830 including mechanical fit, such as a snap-fit. The engagement between the parts 810, 830 can be similar to the engagement shown in FIG. 3.

Similar to the first embodiment, when the cartridge 300 is inserted into the first upper part 810 and the first upper part 810 is mated with the second bottom part 830, the cartridge 300 is in a loaded position.

The dispenser 600 also includes the spray actuator 900 that controls the regulation and spraying of the germicide. In accordance with the present invention, the actuator 900 is in the form of the electronic valve module 500 (see FIG. 3) that includes a controllable valve, the processor (circuit board) 520, the power source 301 and can include the user accessible control switches 20 and the visible indicator lights 30.

As with the first embodiment, the electronic valve module 500 can be a solenoid and therefore, the valve therein is a solenoid valve. The electronic valve module 500 is designed to be coupled directly to the base 700 at a fixed location that is purposely located in relation to the cartridge holder assembly and in particular, the bottom of the bottom part 830. The flow director or valve module housing 560 contains the electronic valve module 500 and has a rear face or surface 502 that includes a coupling member 505 for coupling the module 500 to the base 700. For example, the coupling member 505 can be in the form of a pair of spaced rails that run vertically along and protrude outwardly from the side edges of the rear face 502. The base 700 includes a complementary coupling feature that mates with the coupling member 205 to securely, yet detachably couple the module 500 to the base 700. For example, the base 700 can include a slot 711 that has a pair of side walls 713 that include capturing lips. The side walls 713 extend out perpendicularly from the rear wall of the base 700 and the lips extend inwardly toward one another and are formed at ends of the side walls 713 and are perpendicular to the side walls 713 (parallel to the rear wall of the base 700). Vertical slots are thus formed between the lips and the rear wall and coupling between the module 500 and the base 700 results by inserting the rails 505 of the module housing 560 into the slots defined by the lips and read rear wall of the base. A stop 509 is formed at one end (e.g., bottom end) of the slot 711 and is designed to limit the travel of the module housing 560. In particular, the module 500 is inserted into the top open portion of the slot 711 and then the rails 505 ride within the slots (resulting in a keying action between the two) in a downward direction until the module housing 560 engages the stop 509. The module housing 560 thus rests on the stop 509. As shown, the stop 509 is in the form of a ledge or the like.

As with the previous embodiment, the electronic valve module 500 includes the inlet 540 that receives the liquid or gas, in this case, the discharged germicide, and the opposite outlet 550 with the solenoid valve being formed between the inlet 540 and the outlet 550. The valve module 500 is receive into the hollow flow director/module housing 560 with the outlet 562 (e.g., tubular shaped conduit) receiving the outlet 550 of the module 500 in such a way that the plume of the discharged germicide is not impeded with and more specifically, the outlet 562 and the outlet 550 both have round cavities or spaces that allow for the natural spray pattern of the germicide has it is discharged from the cartridge 300 through the valve of the module 500.

By incorporating the locating and coupling structure directly into the base 700 and by directly coupling the module housing 560 to the base 700, the electronic module 500 can be easily and accurately placed into a desired position relative to the cartridge 300 such that when the cartridge 300 is loaded into the first upper part 810 and the first upper part 810 and second bottom part 830 are mated to form the cartridge holder structure, the valve member 310 of the cartridge 300 engages and seats within the inlet 540 of the electronic module 500. This coupling between the valve member 310 and the inlet 540 of the electronic valve module 500 results in the valve member 310 being moved to the filly opened position, thereby causing germicide to be discharged into the inlet 540. Consequently, once the solenoid valve is opened, the germicide flows into the outlet 550 of the module 500 and is discharged through the outlet of the module housing 560.

Once again as with the first embodiment, once the cartridge 300 is filly loaded into the cartridge holder, the valve assembly 310 is in the actuated on position.

By fixing the cartridge holder to the base 700 and fixing the valve housing 560 to the same base, the interaction between a fully inserted cartridge and the dispenser actuator (in this case, the solenoid valve) can be carefully controlled to provide a system where the user simply has to insert a full cartridge 300 into the cartridge holder and this action results in the accurate seating of the valve member 310 within the electronic valve module 500 and the opening of the valve member 310. Flow of the germicide is thus controlled completely by the position of the solenoid valve which is in response to user inputted (programmed) selections or in response to other events, such as sensing an object, etc. Exemplary operating parameters are outlined in the '418 patent.

The processor (circuit board) 520 can be coupled to the base 700 and can be inserted into another compartment 709 formed in the base 700. Electrical connection is made between the processor 520, the electronic valve module (solenoid) 500 and the power source 301 (batteries), thereby powering the electronic valve module 500 and selectively permit the solenoid valve to be opened and closed depending upon the operating state of the dispenser 100 and based upon the settings selected or programmed by the user. The user accessible control switches 20 and the visible indicator lights 30 are also operatively connected to the processor 520 to permit control over the dispenser and allow the user to place the dispenser 100 in any number of different operating states. A cover 521 with indicia is disposed over the circuit board 520 and identifies the control switches 20 and lights 30.

As with the first embodiment, the controls of the second embodiment of the present invention can include an on/off switch, a reset button, and buttons to set the frequency of when the germicide is sprayed. For example, the one control switch 20 is a switch to set how often the germicide is sprayed and in particular, this switch 20 can be moved into a number of different time interval settings, such as 15 minutes, 30 minutes, and 60 minutes. To program the dispenser 100 to spray every 30 minutes, the control switch 20 is set to the 30 minute setting. The control switches are easily accessible once the front cover 130 is lifted or otherwise separated from the base 200. The indicator lights 30 can include a power on light, a light sensor indicator and a refill indicator that indicates replacement of the cartridge 300 is in order.

In this embodiment, the controls and indicators are located in the upper right corner of the dispenser above the power source (batteries 301).

In yet another aspect of the present invention and similar to the first embodiment, the dispenser 600 has a sensing mechanism 190 incorporated therein to detect the presence of an unintended object underneath or in close proximity to the dispenser 600. When an unintended object is located too close to the dispenser 600 (within the sensing zone), the actuator 500 is not actuated while the unintended object remains within the sensing zone. For example, if a small child is standing underneath or is in close proximity to the dispenser 600, the sensing mechanism will detect such presence and if this detection event overlaps with a time when the dispenser is programmed to be actuated, the dispenser 600 will not spray germicide from the cartridge 300. Instead, the control program can be designed so that if the dispenser 600 is not actuated at the programmed time due to activation of the sensing mechanism, the program will wait a predetermined (programmed) time period before attempting again to actuate the actuator assembly and spray germicide. This process can continue until a successful actuation occurs and the germicide is sprayed.

The sensing mechanism 190 illustrated in the figures includes a pair of sensors that are located at or near the bottom of the dispenser 600. In the illustrated embodiment, the sensing mechanism 190 is located proximate the other control features and PCB 520 of the dispenser 600. In particular and as shown in FIG. 7, the cover 610 can include openings that accommodate the sensors 192. In addition to the sensors 192 themselves, the sensing mechanism 190 also includes a sensor cover 195 that properly locates and positions the sensors 192. The sensor cover 195 includes a pair of slots or notches that receive and hold the sensors at the proper angle. The sensors can be set at 45 degree angles and can be set at different angles from one another resulting in an expanded scope of sensing coverage. The sensors are operatively connected to the electronics (PCB and controller) of the dispenser 600 so that sensor signals are sent to the controller and under select conditions, such as when an unintended object is sensed by sensors 192, the controller controls operation of the actuator 500 so that the unintended object that is located close to the dispenser 600 is not sprayed with germicide. Since there are two sensors, the sensor cover 195 includes two openings to accommodate the sensors. The sensor cover 195 can be snap-fittingly engaged to the cover 610 to allow access to the sensors in the case that access is needed.

Any number of different sensors can be used in the dispenser 600. For example, the sensors can be in the form of motion sensors or can be sensors that detect an obstruction in a path thereof. In one embodiment, the sensing mechanism 190 is configured so that it is capable of sensing an object that is located within one and half feet from the floor to the dispenser 600. This is sufficient to detect a small child or animal, etc.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. A controllable door handle sanitizer comprising:
a base and an outer housing coupled to the base and movable between an open and a closed position;
a holder that receives and holds a container that stores a germicide and includes a first valve member, the holder being coupled to the base such that when the outer housing is opened, the container can be inserted and removed; and
an electronic valve module that includes a housing that is coupled to the base by engaging locating and support members integrally formed as part of the base, the module being positioned relative to the holder such that when the container is in a fully loaded position with respect to the holder, the first valve member is actuated and opened, whereby discharge of the germicide from the sanitizer is determined by an operating state of a second valve member of the electronic valve module that is located downstream of the first valve member.

2. The controllable sanitizer of claim 1, wherein the holder comprises:
an inner sleeve member that receives a bottom of the container and includes an opening at a partially open bottom thereof to allow the first valve member to pass therethrough, the inner sleeve member having at least one locking tab, wherein the inserted container is securely held within the inner sleeve member; and an outer sleeve member that receives the inner sleeve member into an interior thereof and includes an opening at a partially open bottom thereof to allow the first valve member to pass therethrough, the outer sleeve member having a complementary locking mechanism that selectively engages the locking tab resulting in the inner sleeve member being securely yet releasably engaged to the outer sleeve member and the first valve member extends below the outer sleeve member.

3. The controllable sanitizer of claim 2, wherein the inner sleeve member and outer sleeve member each comprises a hollow body and the locking mechanism comprises a locking rail that includes teeth that mate with the locking tab to interlockingly engage the inner sleeve member with the outer sleeve member.

4. The controllable sanitizer of claim 3, wherein the locking tab acts as a pawl and the outer sleeve member includes a receiving notch for initially receiving the locking tab before the locking tab interlockingly mates with the teeth by rotation of the inner sleeve member relative to the outer sleeve member, the receiving notch being disposed adjacent the locking rail.

5. The controllable sanitizer of claim 1, further including a controller that is operatively connected to a power source and to the electronic valve module for controlling the operation thereof, the controller having a housing that is coupled to the base and has an interior space that receives both the electronic valve module and at least the first valve member of the cartridge, wherein in the fully loaded position when the first valve member is permanently actuated, the first valve member is disposed within an inlet of the electronic control module.

6. The controllable sanitizer of claim 5, wherein the electronic valve module includes a flow director that has a hollow interior that receives the electronic valve module and includes an outlet that extends below the controller and is axially aligned with a bottom opening formed in the outer housing to permit the germicide to be discharged from the sanitizer in a generally downward direction toward the door handle.

7. The controllable sanitizer of claim 5, wherein the controller includes a printed circuit board and a sensing mechanism for sensing whether an object is in close proximity to an outlet through which the germicide is discharged, the sensing mechanism being in communication with the controller such that if the object is detected, the electronic valve module is prevented from operating.

8. The controllable sanitizer of claim 7, wherein the sensing mechanism includes a pair of sensors that are disposed at an angle relative to a vertical axis of the sanitizer, the sensors being located at or proximate a bottom of the outer housing such that a range of vision of the sensor extends downwardly from the sanitizer.

9. The controllable sanitizer of claim 7, wherein at least one sensor is disposed at a 45 degree angle relative to the vertical axis.

10. The controllable sanitizer of claim 1, wherein the second valve member comprises a solenoid valve that is located between an inlet of the electronic valve module that receives the first valve member and the germicide discharged therethrough and an outlet that is in communication with an outlet of the sanitizer through which the germicide is discharged.

11. A controllable door handle sanitizer comprising:
a base and an outer housing coupled to the base and movable between an open and a closed position;
a holder that receives and holds a container that stores a germicide, the container having a first valve member, the holder being coupled to the base such that when the outer housing is opened, the container can be inserted and removed;
an electronic valve module that includes a housing that is coupled to the base, the module being positioned relative to the holder such that when the container is in a fully loaded position with respect to the holder and the holder is disposed in a loaded position within the base, the first valve member is placed in fluid communication with the electronic valve module;
an inner sleeve member that receives a bottom of the container such that the container is securely held within the inner sleeve member and includes an opening at a partially open bottom thereof to allow the first valve member to pass therethrough;
an outer sleeve member that receives the inner sleeve member into an interior thereof and includes an opening at a partially open bottom thereof to allow the first valve member to pass therethrough, the outer sleeve member having a locking mechanism that selectively engages a portion of the inner sleeve member to provide a releasable engagement between the inner and outer sleeve members, thereby allowing removal of the cartridge from the housing, the outer sleeve member being coupled to the housing with the partially open bottom of the outer sleeve member being disposed proximate to electronic valve module; and
a controller including a power source for controlling operation of the sanitizer, the electronic valve module being operatively coupled to the controller such that the controller selectively signals the second valve member to open and close depending upon on user inputted operating selections that control when the germicide is discharged.

12. A controllable door handle sanitizer comprising:
a base and an outer housing coupled to the base and movable between an open and a closed position;
a holder that receives and holds a container that stores a germicide and includes a first valve member, the holder being coupled to the base such that when the outer housing is opened, the container can be inserted and removed;
an electronic valve module that includes a housing that is coupled to the base, the module being positioned relative to the holder such that when the container is in a fully loaded position with respect to the holder and the holder is disposed in a loaded position within the base, the first valve member is actuated and opened, whereby discharge of the germicide from the sanitizer is determined by an operating state of a second valve member of the electronic valve module that is located downstream of the first valve member and in fluid communication thereof; and
a controller including a power source for controlling operation of the sanitizer, the electronic valve module being operatively coupled to the controller such that the controller selectively signals the second valve member to open and close depending upon on user inputted operating selections that control when the germicide is discharged.

* * * * *